US011045666B2

(12) United States Patent
Bossier et al.

(10) Patent No.: US 11,045,666 B2
(45) Date of Patent: Jun. 29, 2021

(54) PARTICLE THERAPY SYSTEM WITH ROTATING BEAM DELIVERY

(71) Applicant: Ion Beam Applications S.A., Louvain-la-Neuve (BE)

(72) Inventors: Vincent Bossier, Louvain-la-Neuve (BE); Yves Claereboudt, Louvain-la-Neuve (BE); Guillaume Janssens, Louvain-la-Neuve (BE); Olivier De Wilde, Louvain-la-Neuve (BE); David Vangeenberghe, Louvain-la-Neuve (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 16/654,049

(22) Filed: Oct. 16, 2019

(65) Prior Publication Data

US 2020/0121955 A1  Apr. 23, 2020

(30) Foreign Application Priority Data

Oct. 17, 2018  (EP) .................................... 18200961

(51) Int. Cl.
*A61N 5/10* (2006.01)

(52) U.S. Cl.
CPC ......... *A61N 5/1065* (2013.01); *A61N 5/1069* (2013.01); *A61N 5/1081* (2013.01);
(Continued)

(58) Field of Classification Search
CPC .. A61N 5/1065; A61N 5/1069; A61N 5/1081; A61N 2005/1074;
(Continued)

(56) References Cited

U.S. PATENT DOCUMENTS 7,834,336 B2   11/2010  Boeh et al.
2010/0322381 A1*  12/2010  Stahl ................... A61N 5/1042
378/65

(Continued)

FOREIGN PATENT DOCUMENTS

EP        2 266 664       12/2010
WO   WO-2011/084878       7/2011
(Continued)

OTHER PUBLICATIONS

Extended European Search Report dated May 10, 2019, in counterpart European Application No. 18200961.3; 7 pages.

*Primary Examiner* — Marcus H Taningco
(74) *Attorney, Agent, or Firm* — Finnegan, Henderson, Farabow, Garrett & Dunner LLP

(57) ABSTRACT

A particle therapy system includes a particle accelerator for generating a charged particle beam, a beam delivery device, a beam transport system for transporting the beam from the particle accelerator to the beam delivery device, and a supporting device for supporting a subject. The beam delivery device is rotatable around the target and with respect to the supporting device, so as to be able to deliver the beam to the target according to a plurality of irradiation angles. The system also includes a controller configured to make the beam delivery device rotate at a beam-on speed and meanwhile to irradiate the target with the beam. The controller is configured to make the beam delivery device rotate at at least two different beam-on speeds with respect to the supporting device, a first speed corresponding to a first irradiation angle and a second speed corresponding to a second irradiation angle.

12 Claims, 2 Drawing Sheets

Figure 1:
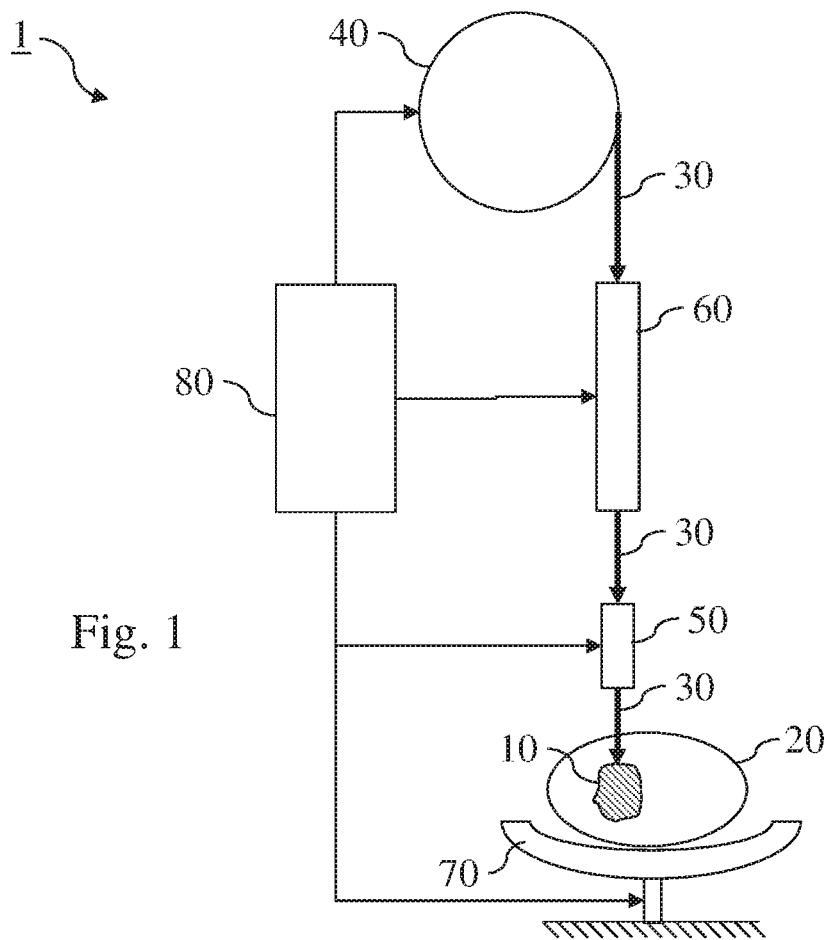

(52) U.S. Cl.
CPC ............... *A61N 2005/1074* (2013.01); *A61N 2005/1087* (2013.01)

(58) Field of Classification Search
CPC .......... A61N 2005/1087; A61N 5/1047; A61N 5/1043; A61N 5/1042; A61N 5/1077; A61N 2005/1092
See application file for complete search history.

(56) References Cited

U.S. PATENT DOCUMENTS

| | | |
|---|---|---|
| 2014/0275701 A1 | 9/2014 | Peltola et al. |
| 2018/0133518 A1* | 5/2018 | Harper ................. A61N 5/1081 |
| 2020/0197727 A1* | 6/2020 | Liu ....................... A61N 5/1084 |

FOREIGN PATENT DOCUMENTS

| | | |
|---|---|---|
| WO | WO-2018/031365 | 2/2018 |
| WO | WO-2018/083072 | 5/2018 |

* cited by examiner

PARTICLE THERAPY SYSTEM WITH ROTATING BEAM DELIVERY

FIELD OF THE PRESENT DISCLOSURE

The present disclosure relates to charged particle therapy systems, such as proton therapy systems for example, and more particularly to charged particle therapy systems wherein a charged particle beam delivery device is rotating with respect to the target of a subject to be treated while delivering the charged particle beam to said target, and/or wherein a device supporting said subject is rotating with respect to the charged particle beam delivery device while delivering the charged particle beam to said target.

In exemplary cases, such systems are sometimes referred to as Spot-scanning Proton ARC or Scanned Proton ARC (SPARC) systems, or to SPARC therapy in case one refers to the corresponding treatment method.

DESCRIPTION OF PRIOR ART

Particle therapy such as proton therapy for example is well known in the art and it has the possibility to improve the quality of the treatment by enhancing the dose conformity at the target (tumor) level while reducing the total dose received by the subject (the patient). By better shaping the tumor dose it can further reduce dose to critical organs. In addition, the SPARC therapy technique increases the robustness of the treatment plan, and may further improve the adoption of dose escalation and hypo-fractionation.

SPARC systems and methods are known from U.S. Pat. No. 7,834,336B2 for example.

This patent discloses a method of irradiating a target in a subject using charged particle therapy and comprising the steps of positioning a subject on a supporting device, positioning a delivery device adapted to deliver charged particles, and delivering charged particles to a target in the subject, wherein the delivery device rotates around the target during delivery of at least a portion of the charged particles.

Though such system works well, there is room for improvement in the way the system operation is controlled.

SUMMARY

It is an object of the present disclosure to solve at least partially the problems of the state of the art. It is more particularly an object of the present disclosure to reduce the treatment time of the subject.

The present disclosure is defined by the independent claims. The dependent claims define advantageous embodiments.

According to the present disclosure, there is provided a particle therapy system for irradiating a target of a subject with a charged particle beam, said particle therapy system comprising:
- a particle accelerator for generating the charged particle beam,
- a beam delivery device for delivering the charged particle beam to the target,
- a beam transport system for transporting the charged particle beam from the particle accelerator to the beam delivery device,
- a supporting device for supporting the subject,
- the beam delivery device being rotatable around the target and with respect to the supporting device and/or the supporting device being rotatable with respect to the beam delivery device, so as to be able to deliver the charged particle beam to the target according to a plurality of irradiation angles,
- a controller configured to make the beam delivery device rotate at a beam-on speed around the target and with respect to the supporting device and/or to make the supporting device rotate at a beam-on speed with respect to the beam delivery device and to meanwhile irradiate the target with the charged particle beam, wherein the controller is configured to make the beam delivery device rotate around the target at at least two different and non-zero beam-on speeds with respect to the supporting device, a first beam-on speed corresponding to a first irradiation angle and a second beam-on speed corresponding to a second irradiation angle among the plurality of irradiation angles, and/or wherein the controller is configured to make the supporting device rotate at at least two different and non-zero beam-on speeds with respect to the beam delivery device, a third beam-on speed corresponding to the first irradiation angle and a fourth beam-on speed corresponding to the second irradiation angle among the plurality of irradiation angles.

With such a system, one can indeed control the beam delivery device and/or the supporting device so that they rotate at different rotation speeds at or around different irradiation angles and hence reduce a treatment time. A smaller treatment time is more comfortable for the patient and also enables to treat more patients in a day. If the irradiation of a first field corresponding to a first irradiation angle requires for example less time than the time needed to irradiate a second field corresponding to a second irradiation angle, the controller may increase the beam-on speed (i.e. the rotation speed of the beam delivery device and/or of the supporting device while irradiating the target) when the beam delivery device and/or the supporting device is at or around the first irradiation angle.

The beam delivery device is rotatable around the target and with respect to the supporting device. The beam delivery device is mounted on a gantry, the gantry being rotatable with respect to the supporting device.

The supporting device may also be rotatable with respect to the beam delivery device.

The controller may be configured to irradiate the target with the charged particle beam according to a plurality of irradiation fields, each irradiation field of said plurality of irradiation fields corresponding respectively to a specific irradiation angle among the plurality of irradiation angles. An irradiation field corresponding to a specific irradiation angle is for example an irradiation field selected by a medical doctor for said specific irradiation angle and it is inputted into the system.

In some examples, system parameters for each irradiation field are provided by a treatment planning subsystem which may or may not be part of the controller. The controller then sets all system parameters so that, when in operation, the system irradiates said field to the target when the beam delivery device and/or the supporting device is at or around the corresponding irradiation angle.

In some embodiments, for at least one irradiation angle among the plurality of irradiation angles, the beam-on speed depends on a time required for irradiating the target with the irradiation field corresponding to said at least one irradiation angle. In further embodiments, the said beam-on speed is inversely proportional to the said time for irradiating the target with the irradiation field corresponding to said at least one irradiation angle. Indeed, the smaller the required irradiation time, the higher beam-on speed can be used.

SHORT DESCRIPTION OF THE DRAWINGS

Figure 2:
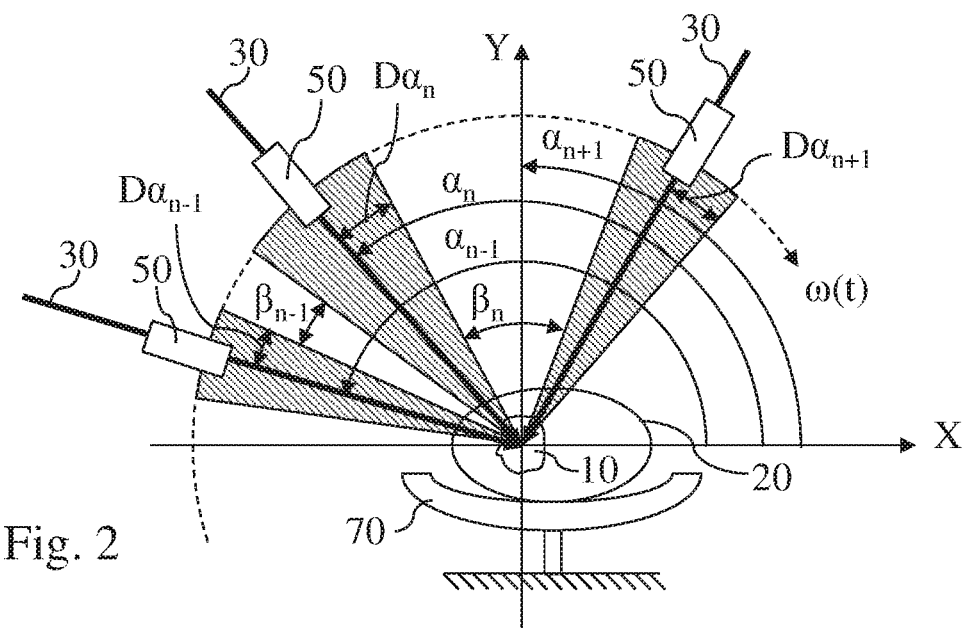
Figure 3:
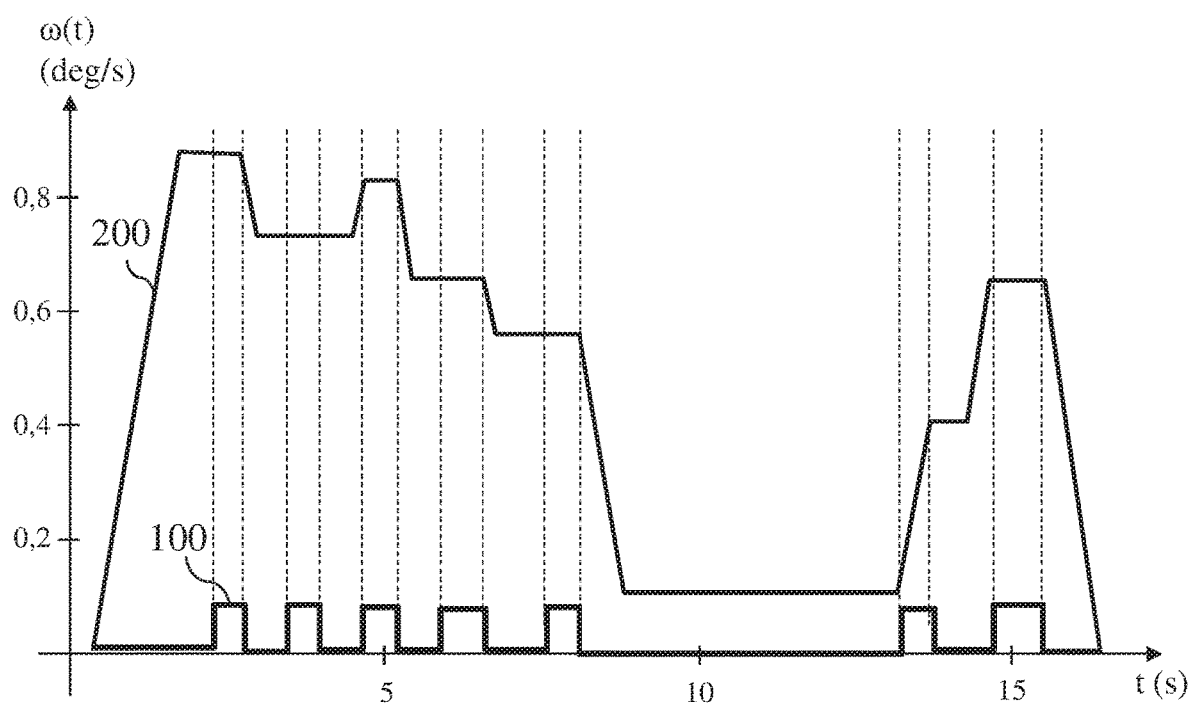

These and further aspects of the present disclosure will be explained in greater detail by way of examples and with reference to the accompanying drawings in which:

FIG. 1 schematically shows a particle therapy system according to the present disclosure;

FIG. 2 schematically shows an exemplary beam delivery device according to an embodiment of the present disclosure;

FIG. 3 shows exemplary curves of the rotation speed of the beam delivery device and of the ON/OFF status of a particle beam of a system according to the present disclosure.

The drawings of the figures are neither drawn to scale nor proportioned. Generally, similar or identical components are denoted by the same reference numerals in the figures.

DETAILED DESCRIPTION

FIG. 1 schematically shows a particle therapy system according to the present disclosure. It is basically a particle therapy system for irradiating a target of a subject with a charged particle beam. The particle therapy system comprises:
- a particle accelerator for generating the charged particle beam,
- a beam delivery device for delivering the charged particle beam to the target,
- a beam transport system for transporting the charged particle beam from the particle accelerator to the beam delivery device,
- a supporting device for supporting the subject.

The beam delivery device (50) is rotatable around the target (10) and with respect to the supporting device (70) so as to be able to deliver the charged particle beam (30) to the target (10) according to a plurality of irradiation angles ($\alpha$) (first embodiment). Alternatively (second embodiment) or additionally (third embodiment), the supporting device (70) is rotatable with respect to the beam delivery device (50) so as to be able to deliver the charged particle beam (30) to the target (10) according to a plurality of irradiation angles ($\alpha$).

The particle therapy system (1) also comprises a controller (80) configured to make the beam delivery device (50) rotate at a beam-on speed around the target (10) and with respect to the supporting device (70) and/or to make the supporting device (70) rotate at a beam-on speed with respect to the beam delivery device (50) and to meanwhile irradiate the target (10) with the charged particle beam (30).

Such a configuration is well known in the art and is for example described in U.S. Pat. No. 7,834,336B2 which is incorporated herein in its entirety by reference.

Specific to the present disclosure is that the controller (80) is configured to make the beam delivery device (50) rotate around the target (10) at at least two different and non-zero beam-on speeds with respect to the supporting device (70), a first beam-on speed corresponding to a first irradiation angle ($\alpha 1$) and a second beam-on speed corresponding to a second irradiation angle ($\alpha 2$) among the plurality of irradiation angles ($\alpha$), and/or in that the controller (80) is configured to make the supporting device (70) rotate at at least two different and non-zero beam-on speeds with respect to the beam delivery device (50), a third beam-on speed corresponding to the first irradiation angle ($\alpha 1$) and a fourth beam-on speed corresponding to the second irradiation angle ($\alpha 2$) among the plurality of irradiation angles ($\alpha$).

First Embodiment

A first embodiment of a particle therapy system (1) according to the present disclosure will now be described in more detail. In this first embodiment, the controller (80) is configured to make the beam delivery device (50) rotate around the target (10) at at least two different and non-zero beam-on speeds with respect to the supporting device (70), a first beam-on speed corresponding to a first irradiation angle ($\alpha 1$) and a second beam-on speed corresponding to a second irradiation angle ($\alpha 2$) among the plurality of irradiation angles ($\alpha$), while the target (10) is being irradiated with the charged particle beam (30) and while the supporting device (70) is kept stationary or is performing a translational motion.

FIG. 2 schematically shows an exemplary beam delivery device (50) according to the first embodiment of the present disclosure.

On this figure one can see that the beam delivery device (50) is rotated around the target (10) at a beam-on speed $\omega(t)$ in function of time, while the supporting device (70) and hence the subject (20) are kept stationary during the treatment. Three exemplary angular positions occupied by the beam delivery device (50) in the course of its rotation are shown, respectively at three irradiation angles $\alpha_{n-1}$, $\alpha_n$ and $\alpha_{n+1}$. It is to be noted that these three angular positions may be occupied at various instants and that they are not necessarily successive. In other words, the beam-on speed may be positive (clockwise) or negative (anti-clockwise) or a mix of both. The beam-on speed may always clockwise or always anti-clockwise in the course of one treatment of the subject (20).

The controller (80) is configured to make the beam delivery device (50) rotate around the target (10) at at least two different and non-zero beam-on speeds with respect to the supporting device (70), a first beam-on speed $\omega$ (t1) corresponding to a first irradiation angle ($\alpha 1$), and a second beam-on speed $\omega(t2)$ corresponding to a second irradiation angle ($\alpha 2$), while the target (10) is being irradiated with y the charged particle beam (30). The first beam-on speed $\omega(t1)$ is for example the rotation speed of the beam delivery device (50) when the beam delivery device (50) is at the angle $\alpha_n$. The second beam-on speed $\omega(t2)$ is for example the rotation speed of the beam delivery device (50) when the beam delivery device (50) is at the angle $\alpha_{n+1}$.

To make the beam delivery device (50) rotate, it may for example be motorized. The beam delivery device (50) may be mounted on a gantry, the gantry being rotatable around the target (10) and with respect to the supporting device (70). Such rotating gantries are well known in the art of particle therapy system (1)s. An exemplary gantry is an isocentric gantry. An exemplary beam delivery device (50) is sometimes called a nozzle.

The controller (80) may be configured to irradiate the target (10) with the charged particle beam (30) according to a plurality of irradiation fields, each irradiation field of said plurality of irradiation fields corresponding respectively to a specific irradiation angle ($\alpha$) among the plurality of irradiation angles ($\alpha$). As such, this is also known in the art. Specific to the present disclosure is however that the controller (80) is configured in such a way that two different irradiation fields among said plurality of irradiation fields are delivered to the target (10) while the beam delivery device (50) is respectively rotated around the target (10) at two different beam-on speeds. In the example of FIG. 2, a first irradiation field is for example delivered to the target (10) while the beam delivery device (50) is rotated at the first beam-on speed ω(t1) when the beam delivery device (50) is at and or also around the angle $\alpha_n$, and a second irradiation field is for example delivered to the target (10) while the beam delivery device (50) is rotated at the second beam-on speed ω(t2), different from ω(t1), when the beam delivery device (50) is at and or also around the angle $\alpha_{n+1}$.

An irradiation field corresponding to a specific irradiation angle (α) is for example an irradiation field selected by a medical doctor for said specific irradiation angle (α) and it is inputted into the system. Generally, system parameters for each irradiation field are provided by a treatment planning subsystem which may or may not be part of the controller (80). The controller (80) then sets all system parameters so that, when in operation, the system irradiates said field to the target (10) when the beam delivery device (50) and/or the supporting device (70) is at or around the corresponding irradiation angle (α).

In some embodiments, the controller (80) is configured such that, for at least one irradiation angle (α) among the plurality of irradiation angles (α), the beam-on speed depends on a time for irradiating the target (10) with the irradiation field corresponding to said at least one irradiation angle (α). In the case of a particle therapy system (1) configured for irradiating the target (10) layer by layer with the known spot-scanning technique for example, the said time for irradiating the target (10) is the time needed for irradiating all spots of all layers of said irradiation field, which may also include a time needed for tuning the particle beam (30).

In some embodiments, the said beam-on speed is inversely proportional to the said time for irradiating the target (10) with the irradiation field corresponding to said at least one irradiation angle (α). Indeed, the smaller the required irradiation time, the higher beam-on speed can be used.

In some embodiments, the controller (80) is configured such that, for said at least one irradiation angle (α) among the plurality of irradiation angles (α), the beam-on speed further depends on a system-specific minimum rotation speed of the beam delivery device (50) with respect to the supporting device (70). A system-specific minimum rotation speed of the beam delivery device (50) is for example a speed under which the particle therapy system (1) would not operate under required conditions for particle therapy or would not operate at all. A system-specific minimum rotation speed of the beam delivery device (50) is for example the minimum rotation speed under which a speed controller (80) does not operate.

More specifically, the controller (80) may be configured such that the beam-on speed is higher or equal to the said system-specific minimum rotation speed of the beam delivery device (50), at any and all irradiation angles (α). The beam-on speed is here to be regarded as the instantaneous rotation speed of the beam delivery device (50) around the target (10) when the beam delivery device (50) is at any and all irradiation angles (α).

In some embodiments, the controller (80) may be configured such that, for said at least one irradiation angle (α) among the plurality of irradiation angles (α), the beam-on speed further depends on a system-specific maximum rotation speed of the beam delivery device (50) with respect to the supporting device (70).

A system-specific maximum rotation speed of the beam delivery device (50) is for example a speed over which the particle therapy system (1) would not operate under required conditions for particle therapy, or simply a limit speed which the system can't exceed for physical reasons (maximum speed of a driving motor for example). More specifically, the controller (80) may be configured such that the beam-on speed is less than or equal to the said system-specific maximum rotation speed of the beam delivery device (50), at any and all irradiation angles (α). The beam-on speed is here to be regarded as the instantaneous rotation speed ω(t) of the beam delivery device (50) around the target (10).

In some examples or for at least one irradiation angle (α), the controller (80) is further configured to keep the beam-on speed constant while irradiating the target (10) with at least one irradiation field of said plurality of irradiation fields. In other examples or for at least another irradiation angle (α), the controller (80) is configured to vary the beam-on speed while irradiating the target (10) with at least one irradiation field of said plurality of irradiation fields.

Referring to FIG. 2, and to the case where the controller (80) is configured to irradiate the target (10) with the charged particle beam (30) according to a plurality of irradiation fields, each irradiation field of said plurality of irradiation fields corresponds respectively to a specific irradiation angle (α) among the plurality of irradiation angles (α). As is known in the art, irradiation of the target (10) with an irradiation field may be performed while the angular position of beam delivery device (50) is within a limited range of angles before and/or after an irradiation angle (α) $\alpha_i$. This limited range of angular positions will hereafter be named a tolerance window. In the example of FIG. 2, irradiation of a field corresponding to irradiation angle (α) an may for example be performed while the beam delivery device (50) rotates in a tolerance window whose boundaries are defined by angular positions $(\alpha_n - D\alpha_n)$ and $(\alpha_n + D\alpha_n)$.

Such a tolerance $D\alpha_n$ results for example from clinical requirements and may serve as an input to the controller (80). The same holds for the other irradiation angles (α). As said before, another input to the controller (80) may be the time required for irradiating the target (10) with the irradiation field corresponding to said at least one irradiation angle (α).

In some examples, the controller (80) receives or calculates, for each irradiation angle (α) $\alpha_i$ among the plurality of irradiation angles (α): the corresponding irradiation field to be delivered to the target (10), a tolerance $D\alpha_i$ on the irradiation angle (α) $\alpha_i$, and a time $t_i$ required for irradiating the target (10) with the irradiation field corresponding to the irradiation angle (α) $\alpha_i$. On the basis of these parameters, the controller (80) then calculates a beam-on speed which may for example be equal to $\omega(t) = 2 \cdot D\alpha_i / t_i$ (in rad/s) for the irradiation angle $\alpha_i$. The controller (80) may then turn the particle beam (30) ON when the beam delivery device (50) reaches or is at angular position $(\alpha_i - D\alpha_i)$ and turn the beam (30) OFF when the beam delivery device (50) is at position $(\alpha_i + D\alpha_i)$.

As said before, the controller (80) may be configured such that the beam-on speed is higher or equal to a system-specific minimum rotation speed of the beam delivery device (50). In this case, an additional input to the controller (80) is the said system-specific minimum rotation speed of the beam delivery device (50). When it turns out that the value of $2 \cdot D\alpha_i / t_i$ s smaller than said system-specific minimum rotation speed, the controller (80) may for example halt the rotation of the beam delivery device (50) for a while.

As said before, the controller (80) may be configured such that the beam-on speed is lower than or equal to a system-specific maximum rotation speed of the beam delivery device (50). In this case, an additional input to the controller (80) is the said system-specific maximum rotation speed of the beam delivery device (50). When it turns out that the value of $2 \cdot D\alpha_i/t_i$ s larger than said system-specific maximum rotation speed, the controller (80) may for example reduce the value of $D\alpha_i$ which was previously received or calculated to a smaller value $D\alpha_{is}$ and turn the particle beam (30) ON when the beam delivery device (50) reaches or is at angular position $(\alpha_n-D\alpha_{is})$ and may turn the beam (30) OFF when the beam delivery device (50) is at position $(\alpha_n+D\alpha_{is})$.

In the above examples, the beam (30) is kept ON while the beam delivery device (50) is at angular positions which are symmetrically arranged around the irradiation angle ($\alpha$) $\alpha_i$, but an asymmetric behaviour may of course also be used, provided one remains within the clinical acceptable range of angular positions before and/or after irradiation angle ($\alpha$) $\alpha_i$.

In some embodiments, the controller (80) is configured to find the highest beam-on speed that allows to deliver the complete irradiation field associated to a given irradiation angle ($\alpha$) within the associated tolerance window.

There are two exemplary strategies, depending on the performance of the feedback reading on the rotation speed of the beam delivery device (50).

Strategy A considers that the read out is too slow and in this case the controller (80) precomputes all the speed parameters.

Strategy B assumes that the read out performance is compatible with a real-time speed regulation of the beam delivery device (50) by the controller (80).

Strategy A

Before the irradiation of the target (10) starts, the following parameters are computed by or transmitted to the controller (80):

Beam-on speed for each irradiation angle ($\alpha$).
Beam-off speed=the rotation speed of the beam delivery device (50) between two successive irradiations.
Start angle for each irradiation field=the angle at which the beam (30) is switched ON.

Once this computation is over, the controller (80) starts the following sequence:
A1/ move the beam delivery device (50) to the first start angle within the tolerance window corresponding to a first irradiation angle ($\alpha$1);
A2/ set the speed of the beam delivery device (50) to the beam-on speed for the current irradiation angle ($\alpha_i$) and switch the particle beam (30) ON;
A3/ deliver the current irradiation field to the target (10);
A4/ once the irradiation field is delivered, set the speed of the beam delivery device (50) to the beam-off speed:
A5/ If the last irradiation field is delivered, then STOP, else wait for the next start angle to be reached and Goto step A2.

Strategy B

In strategy B, the same steps A1 to A5 are performed by the controller (80), but additional steps of computing the beam-on speed, the beam-off speed and the start angle are for example performed during step A1 and/or while the beam delivery device (50) is moving at the previous beam-off speed.

In some embodiments, the controller (80) is further configured to make the beam delivery device (50) rotate at a beam-off speed with respect to the supporting device (70) and meanwhile to stop irradiating the target (10) with the charged particle beam (30), and more specifically to make the beam delivery device (50) rotate at at least two different and non-zero beam-off speeds with respect to the supporting device (70), a first beam-off speed corresponding to a first irradiation angle ($\alpha$1) and a second beam-off speed corresponding to a second irradiation angle ($\alpha$2) among the plurality of irradiation angles ($\alpha$). The rotation speed of the beam delivery device (50) may be varied in-between the delivery of irradiation fields, namely when the particle beam (30) is switched OFF. One may for example accelerate or decelerate the rotation speed of the beam delivery device (50) in order to prepare for the next beam-on speed and/or in order to have enough time or just enough time to change an energy of the particle beam (30), as will become apparent when discussing FIG. 3 and further discussing FIG. 2 for example. The beam-off speed corresponding to a given irradiation angle ($\alpha$) is the average rotation speed of the beam delivery device (50) over the time period starting at the end of the irradiation (beam (30) is switched OFF) corresponding to said given irradiation angle ($\alpha$) and ending at the start of the irradiation corresponding to the next irradiation angle ($\alpha$) (beam (30) is switched ON again).

In some embodiments, the controller (80) is further configured to change an energy of the particle beam (30) to be delivered to the target (10) while the beam delivery device (50) rotates at least one of the beam-off speeds. Referring to FIG. 2, the controller (80) may for example change the energy of the particle beam (30) to be delivered to the target (10) while the beam delivery device (50) is at an angular position within the range indicated as $\beta_{n-1}$ and/or $\beta_n$ and/or $\beta_{n+1}$. The controller (80) may be configured to select a beam-off speed which takes into account a time needed to change the energy of the particle beam (30) between two successive irradiation angles ($\alpha$). Specifically, and referring to FIG. 2, the controller (80) is for example configured to receive or to calculate a time $t_{se}$ needed to change the energy of the particle beam (30) between two successive irradiation angles $\alpha_n$ and $\alpha_{n+1}$—namely to change the beam (30) energy from the energy needed at the end of the irradiation corresponding to angle $\alpha_n$ to the energy needed at the beginning of the irradiation corresponding to angle $\alpha_{n+1}$—and to control the rotation speed $\omega(t)$ of the beam delivery device (50) while the angular position of the beam delivery device (50) is within the range indicated as $\beta_n$, in such a way that an average value of $\omega(t)$ over said range is smaller than or equal to $\beta_n/t_{se}$.

The controller (80) may be configured such that the beam-off speed is higher or equal to a system-specific minimum rotation speed of the beam delivery device (50). In this case, an additional input to the controller (80) is the said system-specific minimum rotation speed of the beam delivery device (50). When it turns out for example that the instantaneous value of $\omega(t)$ over a range $\beta_i$ is smaller than said system-specific minimum rotation speed, the controller (80) may for example halt the rotation of the beam delivery device (50) for a while and within the $\beta_i$ range.

The controller (80) may also be configured such that the beam-off speed is lower than or equal to a system-specific maximum rotation speed of the beam delivery device (50). In this case, an additional input to the controller (80) is the said system-specific maximum rotation speed of the beam delivery device (50). When it turns out that an instantaneous value of $\omega(t)$ is larger than said system-specific maximum rotation speed within a $\beta_i$ range, the controller (80) may for example limit the value of $\omega(t)$ to the said system-specific maximum rotation speed of the beam delivery device (50) over the $\beta_i$ range.

FIG. 3 shows exemplary curves of the rotation speed of the beam delivery device (50) and of the ON/OFF status of a particle beam (30) of a particle therapy system according to the present disclosure, when in operation. The upper curve (200) represents the rotation speed ω(t) of the beam delivery device (50) in function of time, expressed in degrees per second. The lower curve (100) represents the ON/OFF status of the particle beam (30) in function of time. The zero value on the lower curve (100) corresponds to the beam (30) being OFF and the non-zero value corresponds to the beam (30) being ON. Each ON state period corresponds to an irradiation angle $\alpha_i$.

The vertical dotted lines allow to clearly see the beam-on speed and the beam-off speed on the upper curve (200) for each irradiation angle ($\alpha_i$). The controller (80) may for example change the energy of the particle beam (30) while the beam (30) is switched OFF.

In some embodiments, the accelerator is a cyclotron or a synchrotron.

In some embodiments, the charged particle beam (30) is a beam of ions, such as protons or carbon ions.

Second Embodiment

In this second embodiment, the controller (80) is configured to make the supporting device (70) rotate at at least two different and non-zero beam-on speeds with respect to the beam delivery device (50), a first beam-on speed corresponding to a first irradiation angle ($\alpha$1) and a second beam-on speed corresponding to a second irradiation angle ($\alpha$2) among the plurality of irradiation angles ($\alpha$), while the target (10) is being irradiated with the charged particle beam (30) and while the delivery device is kept stationary or is performing a translational motion.

To this end, the supporting device (70) may for example be a couch which is mounted on a robotized arm, said robotized arm being adapted to rotate the couch around a Z axis perpendicular to the XY plane in the same referential as the one shown on FIG. 2.

The other parts and way of operation of the particle therapy system (1) are for example the same or equivalent as those described in relation to the first embodiment. In other words, the main difference between the first and the second embodiment is that in the second embodiment the supporting device (70) is rotated with respect to the beam delivery device (50), whereas in the first embodiment the beam delivery device (50) is rotated around the target (10) and with respect to the supporting device (70).

Third Embodiment

In this third embodiment, the controller (80) is configured to make the beam delivery device (50) rotate around the target (10) at at least two different and non-zero beam-on speeds with respect to the supporting device (70), a first beam-on speed corresponding to a first irradiation angle ($\alpha$1) and a second beam-on speed corresponding to a second irradiation angle ($\alpha$2) among the plurality of irradiation angles ($\alpha$), while the target (10) is being irradiated with the charged particle beam (30).

In this third embodiment, the controller (80) is further configured to make the supporting device (70) rotate at at least two different and non-zero beam-on speeds with respect to the beam delivery device (50), a third beam-on speed corresponding to the first irradiation angle ($\alpha$1) and a fourth beam-on speed corresponding to the second irradiation angle ($\alpha$2) while the target (10) is being irradiated with the charged particle beam (30).

This third embodiment therefore corresponds to a combination of the first and the second embodiment, wherein both the beam delivery device (50) and the supporting device (70) rotate while the target (10) is being irradiated with the charged particle beam (30). Various combinations of the first, the second, the third and the fourth beam-on speed are of course possible.

In this third embodiment, the controller (80) may be further configured to make the beam delivery device (50) and/or the supporting device (70) perform a translational motion while they are rotating.

The present disclosure has been described in terms of specific embodiments, which are illustrative of the present disclosure and not to be construed as limiting. More generally, it will be appreciated by persons skilled in the art that the present disclosure is not limited by what has been particularly shown and/or described hereinabove.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

The present disclosure may also be described as follows: a particle therapy system (1) comprising a particle accelerator (40) for generating a charged particle beam (30), a beam delivery device (50) for delivering the beam (30) to a target (10) of a subject (20), a beam transport system (60) for transporting the beam (30) from the particle accelerator (40) to the beam delivery device (50), a supporting device (70) for supporting a subject (20). The beam delivery device (50) is rotatable with respect to the supporting device (70), so as to be able to deliver the beam (30) to the target (10) according to a plurality of irradiation angles ($\alpha$). The system also comprises a controller (80) configured to make the beam delivery device (50) rotate at a beam-on speed and meanwhile to irradiate the target (10) with the beam (30). The controller (80) is configured to make the beam delivery device (50) rotate at at least two different beam-on speeds with respect to the supporting device (70), a first beam-on speed corresponding to a first irradiation angle ($\alpha$1) and a second beam-on speed corresponding to a second irradiation angle ($\alpha$2) among the plurality of irradiation angles ($\alpha$). Having different beam-on speeds enables to reduce the treatment time.

We claim:

1. A particle therapy system for irradiating a target of a subject with a charged particle beam, said particle therapy system comprising:
   a particle accelerator for generating the charged particle beam, wherein the charged particle beam is a beam of ions,
   a beam delivery device for delivering the charged particle beam to the target,
   a beam transport system for transporting the charged particle beam from the particle accelerator to the beam delivery device,
   a supporting device for supporting the subject,
   the beam delivery device being rotatable around the target and with respect to the supporting device and/or the supporting device being rotatable with respect to the beam delivery device, so as to be able to deliver the charged particle beam to the target according to a plurality of irradiation angles,
   a controller configured to:
   control the beam delivery device to rotate at a plurality of beam-on speeds around the target and with respect to the supporting device and/or to control the supporting device to rotate at a plurality of beam-on speeds with respect to the beam delivery device, and to meanwhile irradiate the target with the charged particle beam, wherein the controller is configured to control the beam delivery device to rotate around the target at at least two different and non-zero beam-on speeds with respect to the supporting device, a first beam-on speed corresponding to a first irradiation angle and a second beam-on speed corresponding to a second irradiation angle among the plurality of irradiation angles, and/or wherein the controller is configured to control the supporting device to rotate at least two different and non-zero beam-on speeds with respect to the beam delivery device, a third beam-on speed corresponding to the first irradiation angle and a fourth beam-on speed corresponding to the second irradiation angle among the plurality of irradiation angles;

wherein the controller is further configured to control the beam delivery device to rotate at a plurality of beam-off speeds with respect to the supporting device or vice versa, and to meanwhile stop irradiating the target with the charged particle beam, wherein the controller is further configured to control the beam delivery device to rotate at at least two different and non-zero beam-off speeds with respect to the supporting device or vice versa, a first beam-off speed corresponding to the first irradiation angle and a second beam-off speed corresponding to the second irradiation angle among the plurality of irradiation angles, and wherein the controller is further configured to change an energy of the particle beam to be delivered to the target while the beam delivery device rotates at at least one of the beam-off speeds.

2. A particle therapy system according to claim 1, wherein the beam delivery device is rotatable around the target and with respect to the supporting device.

3. A particle therapy system according to claim 2, wherein the beam delivery device is mounted on a gantry, the gantry being rotatable with respect to the supporting device.

4. A particle therapy system according to claim 1, wherein the supporting device is rotatable with respect to the beam delivery device.

5. A particle therapy system according to claim 1, wherein, for at least one irradiation angle among the plurality of irradiation angles, the beam-on speed depends on a system-specific minimum rotation speed of the beam delivery device with respect to the supporting device or on a system-specific minimum rotation speed of the supporting device with respect to the beam delivery device.

6. A particle therapy system according to claim 5, wherein, for said at least one irradiation angle among the plurality of irradiation angles, the beam-on speed further depends on a system-specific maximum rotation speed of the beam delivery device with respect to the supporting device or on a system-specific maximum rotation speed of the supporting device with respect to the beam delivery device.

7. A particle therapy system according to claim 1, wherein, for at least one irradiation angle among the plurality of irradiation angles, the beam-on speed depends on a system-specific maximum rotation speed of the beam delivery device with respect to the supporting device or on a system-specific maximum rotation speed of the supporting device with respect to the beam delivery device.

8. A particle therapy system according to claim 1, wherein the controller is further configured to keep the beam-on speed constant while irradiating the target with at least one irradiation field of a plurality of irradiation fields, each irradiation field of said plurality of irradiation fields corresponding to a specific irradiation angle among the plurality of irradiation angles.

9. A particle therapy system according to claim 1, wherein the controller is further configured to vary the beam-on speed while irradiating the target with at least one irradiation field of said plurality of irradiation fields, each irradiation field of said plurality of irradiation fields corresponding to a specific irradiation angle among the plurality of irradiation angles.

10. A particle therapy system according to claim 1, wherein the accelerator is a cyclotron or a synchrotron.

11. A particle therapy system according to claim 1, wherein the charged particle beam is a beam of protons or of carbon ions.

12. A particle therapy system according to claim 1, wherein the controller is configured to irradiate the target with the charged particle beam according to a plurality of irradiation fields, each irradiation field of said plurality of irradiation fields corresponding to a specific irradiation angle among the plurality of irradiation angles, wherein the controller receives as input a system-specific maximum rotation speed $\omega max$ of the beam delivery device, wherein, for at least one irradiation angle, the controller receives as input a tolerance window $D\alpha i$ resulting from clinical requirements and a time $ti$ required for irradiating the target with the irradiation field corresponding to said at least one irradiation angle, and wherein the controller is configured such that, if the value of $2 \times D\alpha i/ti$ is larger than $\omega max$, the controller sets the beam-on speed for said at least one irradiation angle to a value of $\omega(t)=2 \times D\alpha is/ti$, wherein $2 \times D\alpha is/ti$ is smaller than or equal to $\omega max$, and the controller turns the particle beam on when the beam delivery device reaches or is at angular position $(\alpha n - D\alpha is)$ and turns the beam off when the beam delivery device is at angular position $(\alpha n + D\alpha is)$.

* * * * *